United States Patent

Andersen et al.

[19]
[11] Patent Number: 5,053,026
[45] Date of Patent: Oct. 1, 1991

[54] ASPIRATING DEVICE

[75] Inventors: Harold W. Andersen, Oyster Bay, N.Y.; Charles H. Harrison, Haw River, N.C.

[73] Assignee: H. W. Andersen Products Inc., Oyster Bay, N.Y.

[21] Appl. No.: 483,528

[22] Filed: Feb. 22, 1990

[51] Int. Cl.⁵ ............................................. A61M 1/00
[52] U.S. Cl. ................................... 604/319; 604/320
[58] Field of Search ............... 604/314, 320, 319, 31, 604/28, 65, 35; 137/624.14, 907, 505.36, 225

[56] References Cited

U.S. PATENT DOCUMENTS

| | | | |
|---|---|---|---|
| 1,636,919 | 7/1927 | Miller | 137/505.36 |
| 4,245,637 | 1/1981 | Nichols | 604/320 |
| 4,669,361 | 6/1987 | Ito et al. | 137/907 |
| 4,671,786 | 6/1987 | Krug | 604/319 |

Primary Examiner—Randall L. Green
Assistant Examiner—Robert Clarke
Attorney, Agent, or Firm—Jordan and Hamburg

[57] ABSTRACT

An aspirating device for removing fluids from a body site includes a container for collecting aspirated fluids, a suction device in communication with the container for applying a negative pressure to the container, a tube connected to the container and adapted to communicate with a body site for transferring fluids from the body site to the container in response to negative pressure in the container, and a valve for controlling the negative pressure in the container, the container having a diaphragmatic wall operable to actuate the valve.

18 Claims, 2 Drawing Sheets

ASPIRATING DEVICE

BACKGROUND OF THE INVENTION

Aspirating devices frequently employ a suction pump, a collection container and a drain tube to facilitate the removal of various fluids from a body cavity, surgical site, or wound site. The drain tube transfers the various fluids from the body site to the collection container under the influence of the vacuum created by a suction pump.

In practice, use of such aspirating devices can result in the transmission of excessive levels of vacuum to the body site. This is to be avoided because the application of high suction levels at the body site can result in injury or damaged tissue adjacent to the area of placement of the drain tube at the body site. In some instances, openings in the drain tube at the body site may come into contact with body tissue thereby blocking off some or all of such openings and resulting in the application of an increased and undesired negative pressure to the body tissue which covers and blocks such openings and risking injury or damage to such tissue.

Attempts have been made to overcome this deficiency. specifically, drain tubes have been designed to provide a vent lumen therein through which fresh air is conducted to the distal end of the tube, thus relieving excessive vacuum. However, there remain innumerable instances where drain tubes not having such a self-relieving features are medically necessitated.

Accordingly, there exists a need for a means of regulating the vacuum of a vacuum pump in an aspirating device to prevent the application of excessive vacuum at the body site to prevent injury at the body site which might otherwise result from said excessive vacuum.

SUMMARY OF THE INVENTION

An object of the present invention is to provide an aspirating device for aspirating body fluids from a body site in a body cavity.

Another object of the present invention is to prevent excessive vacuum at a body site during aspiration thereof and the accompanying injury or tissue damage which might otherwise result from application of such excessive vacuum at the body site.

Another object of the present invention is to provide an aspirating device which effectively regulates the vacuum applied during aspiration of a body site regardless of the design of aspirating tube employed during the aspirating procedure.

Another object is to provide an aspirating device which has high sensitivity to pressure differential.

These and other objects are achieved, in accordance with the present invention, by an aspirating device for removing body fluids from a body site which includes a container means for collecting aspirated body fluids, suction means in communication with the container means for applying negative pressure to the container means, an aspirating tube means connected to the container means and adapted to communicate with a body site for transferring body fluids from the site to the container means in response to the negative pressure, and valve means for regulating the negative pressure in the container means, the container means including a diaphragmatic wall means for actuating the valve means.

Preferably the diaphragmatic wall means is a flexible and resilient bottom wall of the container means. When negative pressure is applied to the container means, the bottom wall deflects inwardly of the container means due to the pressure differential to thereby activate the valve means. Once the negative pressure is removed, the bottom wall, due to its resiliency, automatically returns back to its normal and undeflected state.

BRIEF DESCRIPTION OF THE DRAWINGS

The invention will now be described and will be better understood in conjunction with the accompanying drawings, in which.

DESCRIPTION OF THE PREFERRED EMBODIMENTS

Figure 1:
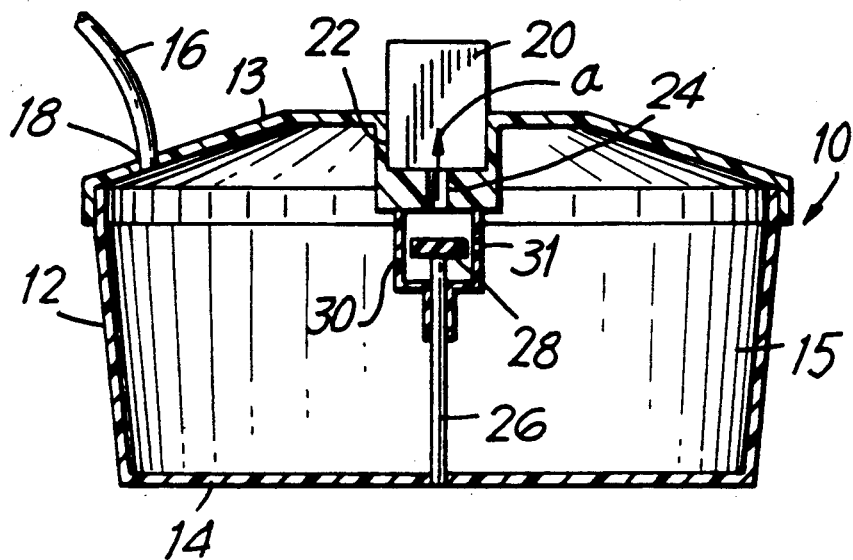
FIG. 1 is a cross-sectional side elevation view of a first embodiment of the suction apparatus of the present invention at the beginning of use.
Figure 2:
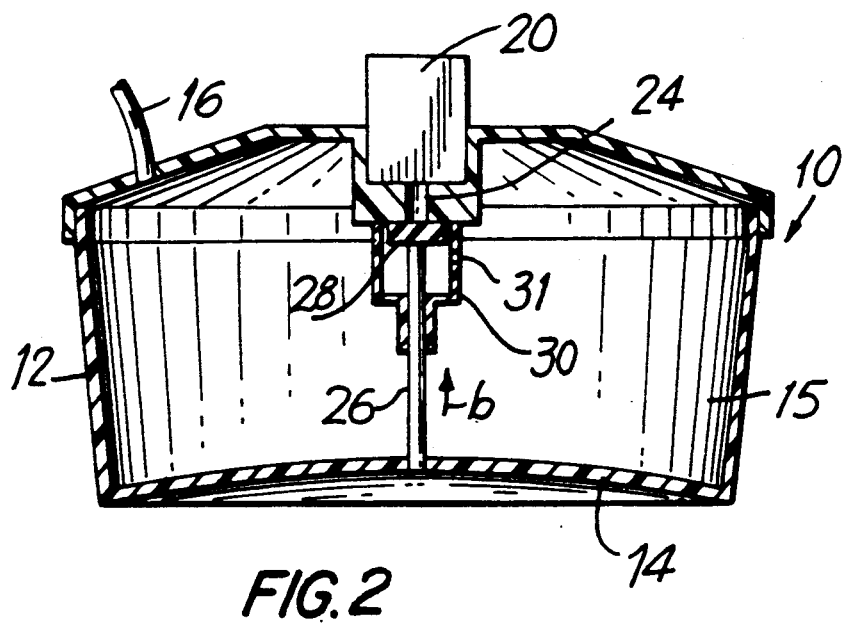
FIG. 2 is a cross-sectional side elevation view similar to FIG. 1 but showing the apparatus in a deflected condition during use.

A first embodiment of the present invention is illustrated in FIGS. 1 and 2. As shown in FIGS. 1 and 2, an aspirating device or suction apparatus of the present invention includes a container, indicated generally at 10, having a side wall 12, a top cover 13, and a diaphragmatic bottom wall 14 defining a sealed interior 15 to the container. An aspirating tube 16 is connected to the cover 13 at 18. Aspirating tube 16 has a non-illustrated distal end which is adapted to be positioned at a wound site or in a patient's body cavity for aspirating body fluids and other fluids from the wound site or cavity and transferring such fluids to the interior 15 of the container 10 as will be described in more detail hereinafter.

An electrically operated air pump or suction unit 20 is arranged in a receptacle 22 on cover 13 to communicate with the interior 15 of the container 10 through a passage 24. When the electrical suction unit 20 is activated, it draws a vacuum through passage 24, as indicated by the arrow a in FIG. 1, thus creating a negative pressure within the container 10 and, correspondingly, within aspirating tube 16. A negative pressure is thus created at the distal end of aspirating tube 16. Accordingly, when the distal end of aspirating tube 16 is positioned at a wound site or in a body cavity, and the electrical suction unit 20 activated, the negative pressure created in tube 16 aspirates fluids from the wound site or body cavity and transfers them to the interior 15 of the container 10.

The suction apparatus of the present invention also includes a valve mechanism for regulating the negative pressure within the container 10. In the embodiment shown in FIGS. 1 and 2, the valve mechanism includes a valve stem 26 connected to diaphragmatic bottom wall 14, valve member 28 connected to stem 26, and a guide slot composed of rigid guide wall 30 for guiding valve stem 26 and valve member 28 as the latter move relative to the passage 24.

Diaphragmatic bottom wall 14 is a semirigid planar wall which is flexible and resilient. It is constructed of a material of sufficient rigidity to withstand a vacuum level applied to the interior 15 of the container 10 by suction unit 20. However, when the vacuum level within the container 10 exceeds a predetermined level, diaphragmatic bottom wall 14 flexes and deforms inwardly of the container. As diaphragmatic bottom wall 14 deflects inwardly, valve stem 26, being connected to diaphragmatic bottom wall 14, is mechanically moved toward passage 24, as shown by arrow b in FIG. 2, until valve member 28 engages the end of passage 24, thus blocking communication between suction unit 20 and the interior 15 of the container and preventing the suction unit 20 from applying further vacuum to the interior 15 of the container. Once the negative pressure within the container drops below the predetermined level, diaphragmatic bottom wall 14, being flexible and resilient, deflects outwardly toward its original position, shown in FIG. 1, thus disengaging valve member 28 from the end of passage 24, whereby passage 24 is opened and negative pressure is again applied to the interior 15 of the container 10 by suction unit 20.

In this way, the negative pressure within the container 10 and applied at the wound site or body cavity through aspirating tube 16 is kept at or below a predetermined level. Diaphragmatic bottom wall 14 thus functions as a means for automatically activating and controlling the valve mechanism when the predetermined level of negative pressure is exceeded. The valve mechanism, composed of valve stem 26 and valve member 28, is activated by the flexure of diaphragmatic bottom wall 14 inwardly to automatically prevent excessive negative pressure within the container 10 and at the body cavity or wound site which would otherwise be transmitted to such site.

Accordingly, by interposing a valve mechanism between the passage 24 through which negative pressure is applied to the interior 15 of container 10 and the diaphragmatic bottom wall 14 of container 10, and by utilizing the mechanical deflection of diaphragmatic bottom wall 14 in response to an internal negative pressure in container 10, the withdrawal of air from the interior 15 of container 10 to the suction unit 20 can be stopped at a vacuum level predetermined by the physical dimensions of the valve mechanism and the semirigid diaphragmatic container construction which acts as an actuating mechanism for the valve mechanism.

Depending on the construction, a sealed container having an internal pressure less than the external or ambient pressure will tend to deflect as a result of the resulting pressure differential even though the deflection may be miniscule. In accordance with the present invention, the diaphragmatic bottom wall 14 is constructed such that it is sufficiently flexible given the vacuum conventionally used in such aspirating devices while the remainder of the container is sufficiently rigid that it can withstand the vacuum resulting from conventionally employed vacuums in such devices. Since the diaphragmatic bottom wall 14 is part of the container, such diaphragmatic bottom wall 14 can be made large and thus more sensitive to pressure differential.

The degree of deflection of diaphragmatic bottom wall 14 and the spatial relationship of valve stem 26 and valve member 28 vis-a-vis passage 24 are selected to achieve the desired objective, i.e., the deflection of the wall material at a given pressure is sufficient to achieve a resultant movement of valve member 28 into engagement with passage 24 to close the passage and prevent the suction unit 20 from applying further vacuum to the interior 15 of the container 10, thus effectively regulating the vacuum applied to the interior 15 of container 10.

The non-diaphragmatic portions of the container can be constructed in various configurations, for example, cylindrical, rectangular or other polygonal shapes of uniform or non-uniform characteristics and dimensions, as long as it is of a sufficiently rigid construction to provide a container capable of withstanding all the forces created by the negative and positive pressures acting on the container when a pressure differential is established between the interior 15 and the exterior of the container 10.

Figure 3:
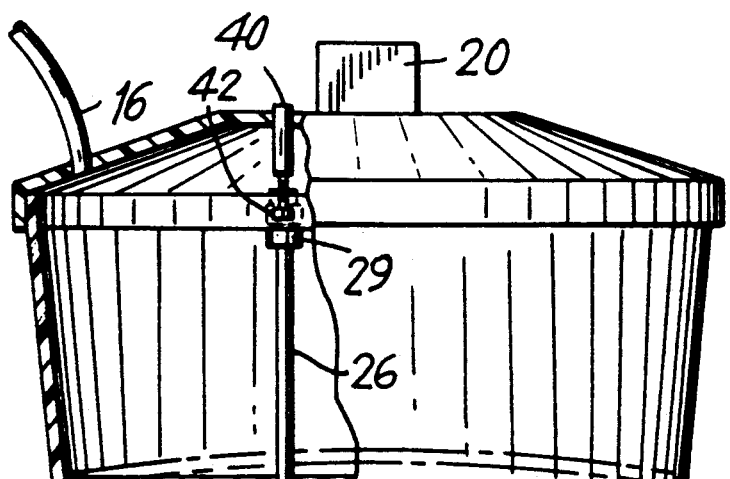
FIG. 3 is a partial cross-sectional side elevation view of a second embodiment of the suction apparatus of the present invention.

FIG. 3 shows another embodiment in which the inward deflection of diaphragmatic bottom wall 14, shown in broken lines, does not move a valve seat into engagement with a vacuum port. In FIG. 3, inward deflection of bottom wall 14 moves valve stem 26 and the end portion 29 of valve stem 26 into engagement with an air valve pin 42 of air valve 40 which communicates with the exterior 15 of container 10. The pressure of end portion 29 against valve pin 42 of air valve 40 opens air valve 40 to allow air from the atmosphere to bleed into the interior 15 of the sealed container 10 to reduce the negative pressure within the container. When the negative pressure in the container does not exceed a selected predetermined level, diaphragramic bottom wall 14 deflects outwardly toward its original configuration, end portion 29 is disengaged from valve pin 42, and air valve 40 closes. By way of example, air valve 40 may be similar to an air valve used in an automobile tire.

Figure 4:
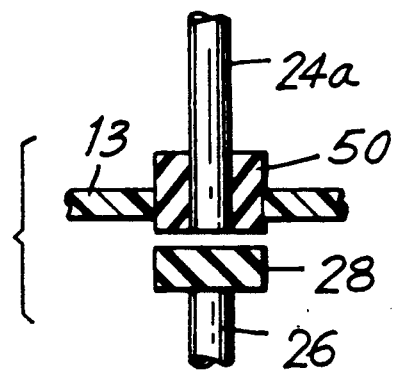
FIG. 4 is an enlarged cross-sectional side view of a modification of the vacuum port of the FIG. 1 embodiment.

FIG. 4 illustrates another embodiment of the present invention in which an electrically operated air pump or suction unit (such as the unit 20 in FIG. 17) is not mounted directly on the cover 13, but is located at a position remote from the container 10. An elongated tube 24a is connected to cover 13 by gasket seal 50, extends outwardly of the container 10, and is connected at an opposite end to a remote suction unit or air pump.

In the embodiment of FIGS. 1 and 2, diaphragmatic bottom wall 14 is constructed as a flat, cylindrical planar area of relatively large dimension which provides a useful deflection depending on the degree of negative pressure applied within the container 10 by suction unit 20. However, physical variations of diaphragmatic bottom wall 14 may be employed within the scope of the present invention.

The deflection of the diaphramatic wall 14 will be greater for a given negative pressure within container 10 for a wall made of a relatively thin material as compared to a wall of a thicker material. Thus, the thickness and flexibility of the bottom wall material may be chosen to provide the desired sensitivity of response, i.e., more or less deflection for a given negative pressure.

Figure 5:
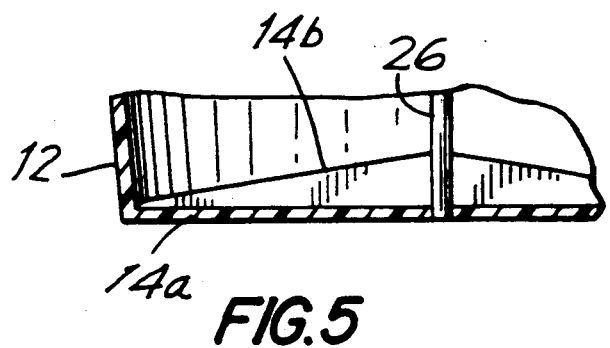
FIG. 5 is a cross-sectional view of an alternative embodiment of the bottom portion of the suction apparatus of the present invention.

For example, as shown in FIG. 5, diaphragmatic bottom wall 14a can be constructed of the same material used to make side wall 12 and cover 13 and may be made integral with the side wall. A relatively thin inner diaphragmatic membrane wall 14b is constructed with spaced ribs 14c. The ribs 14c, or other similar reinforcing material, provide a less flexible construction resulting in less deflection of diaphragmatic bottom wall 14a for a given negative pressure in container 10.

Figure 6:
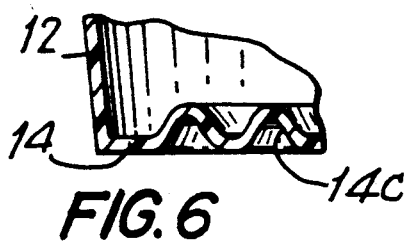
FIG. 6 is a cross-sectional view of another embodiment of the bottom portion of the suction apparatus of the present invention.

FIG. 6 illustrates another embodiment wherein the diaphragmatic bottom wall 14a is provided with a bellows-type outer annular end portion 14a such that the membrane wall 14c is deflected at the bellows-type portion 14c in response to the negative pressure conditions inside container 10. Membrane wall 14c can be constructed to provide a greater and more sensitive deflection for a given negative pressure compared to the diaphragmatic bottom wall 14 of the embodiment of FIGS. 1 and 2.

The suction apparatus of the present invention provides a method of controlling the vacuum in the collection container of a vacuum aspirating device which utilizes the natural flexibility and resiliency of the material of construction of the container itself to actuate the mechanism for controlling the vacuum. Because a part of the container is used as a diaphragmatic control element, the diaphragmatic control element can be made relatively large in area to thereby provide sensitivity in control and regulation of vacuum in the container, eliminating the need for a separate large diaphragm valve to control vacuum.

The aspirating device of the present invention prevents excessive vacuum at the aspiration site, thus preventing damage of tissue adjacent the aspiration tube, insures maintenance of a predetermined vacuum level, provides a built-in termination of vacuum if the aspirating tube should become clogged or blocked, and provides a collection container which is capable of controlling vacuum therein regardless of the particular design of the aspiration drain tube employed, i.e., regardless of whether or not the aspiration tube is self-relieving.

By way of example, the diaphragmatic bottom wall may be made of crystal polystyrene and may have a diameter in the order of eight and one-half inches.

The suction unit 20 may be disposed at another location other than on the cover 13, for example on the side of the container or it may be separated from the container and connected to the container by a conduit.

The diaphragmatic wall may be formed at other locations of the container, for example on the sides of the container or on the cover.

The rigid guide wall 30 may be of a cylindrical construction having one or more holes 31 providing communication between the interior of cylindrical guide wall 30 and the interior of the container. Alternately, the rigid guide wall may be an open support structure having spaced support elements.

Although the present invention has been described through specific terms, it should be noted here that the described embodiment is not necessarily exclusive and that various changes and modifications may be imparted thereto without departing from the scope of the invention, which is limited solely by the appended claims.

What we claim is:

1. An aspirating device for removing fluids from a body site, comprising container means having walls defining a closed chamber for collecting aspirated fluids, suction means in communication with said container means for applying a negative pressure to said container means, tube means connected to said container means and adapted to communicate with a body site for transferring fluids from said body site to said container means in response to negative pressure in said container means, and valve means for controlling the negative pressure in said container means, one of said walls of said container means comprising diaphragmatic wall means operable to actuate said valve means.

2. An aspirating device according to claim 1, wherein said diaphragmatic wall means has an original position occurring when the pressure inside and outside said container means is substantially equal, said diaphragmatic wall means being flexible for flexing inwardly of said container means from said original position to flexed positions when negative pressure is applied to the inside of said container means.

3. An aspirating device according to claim 2, wherein said diaphragmatic wall means is constructed to return from said flexed positions to said original position when negative pressure is no longer applied to the inside of said container means.

4. An aspirating device according to claim 1, wherein said container means has a passageway communicating with the interior of said container means, said suction means comprising a pump having an inlet in communication with said passageway, said valve having an operable member being operable to block and unblock said passageway.

5. An aspirating device according to claim 1, wherein said diaphragmatic wall means has a cylindrical configuration.

6. An aspirating device according to claim 1, wherein said diaphragmatic wall means comprises a diaphragm, said diaphragm having a structure part for controlling the flexure sensitivity of said diaphragm.

7. An aspirating device according to claim 6, wherein said structure part comprises ribs on said diaphragm.

8. An aspirating device according to claim 6, wherein said structure part comprises an undulating bellows structure on at least a portion of said diaphragm.

9. An aspirating device for removing fluids from a body site, comprising container means for collecting aspirated fluids, suction means in communication with said container means for applying a negative pressure to said container means, tube means connected to said container means and adapted to communicate with a body site for transferring fluids from said body site to said container means in response to negative pressure in said container means, and valve means for controlling the negative pressure in said container means, said container means comprising diaphragmatic wall means operable to actuate said valve means, said container means having a bottom wall at least part of which constitutes said diaphragmatic wall means, said bottom wall having an original position when the pressure inside and outside said container means are equal, said bottom wall being flexible for deflecting inwardly of said container means to flexed positions when negative pressure is applied to said container means by said suction means, said bottom wall being resilient for returning to said original position when said negative pressure is no longer applied to said container means by said suction means.

10. An aspirating device according to claim 9, wherein said valve means comprises an elongated stem means mounted on said bottom wall, said stem means being disposed in said container means, said valve means further comprising a valve body having a passageway leading to the interior of said container means, said stem means being operable to close off said passageway when said diaphragmatic bottom wall is in one of its flexed positions.

11. An aspirating device according to claim 10, wherein said suction means comprises a suction pump having an inlet in communication with said passageway such that said suction pump is operable to apply suction to the interior of said container means through said passageway during operation of said suction pump.

12. An aspirating device according to claim 11, wherein said valve body has a valve seat means at one end of said passageway, said stem means having an upper longitudinal end portion, a valve member on said end portion, said valve member being operable to seat on said valve seat means to close off said passageway when said diaphragmatic bottom wall is in one of said one flexed position.

13. An aspirating device according to claim 9, wherein said container means is a sealed side wall extending upright from said bottom wall and a cover means disposed on said side wall, said stem means being disposed in said container means and extending upright from said bottom wall, said valve means being mounted on said cover in a position overlying said stem means, said stem means having an upper longitudinal end portion, and actuating means on said end portion for actuating said valve means.

14. An aspirating device according to claim 12, wherein said diaphragmatic wall means has a stem operable to engage said actuatable member to move said actuatable member from said unactuated position to said actuated position when said diaphragmatic wall means is flexed inwardly due to negative pressure applied to the interior of said container means.

15. An aspirating device for removing fluids from a body site, comprising container means for collecting aspirated fluids, suction means in communication with said container means for applying a negative pressure to said container means, tube means connected to said container means and adapted to communicate with a body site for transferring fluids from said body site to said container means in response to negative pressure in said container means, and valve means for controlling the negative pressure in said container means, said container means comprising diaphragmatic wall means operable to actuate said valve means, said container means having a cover, said valve means being mounted on said cover, said container means having a bottom wall constituting said diaphragmatic wall means, an elongated stem means inside said container means connected to said bottom wall, said stem means underlying said valve means and being operable to actuate said valve means when said diaphragmatic wall means is flexed inwardly of said container means.

16. An aspirating device for removing fluids from a body site, comprising container means for collecting aspirated fluids, suction means in communication with said container means for applying a negative pressure to said container means, tube means connected to said container means and adapted to communicate with a body site for transferring fluids from said body site to said container means in response to negative pressure in said container means, and valve means for controlling the negative pressure in said container means, said container means comprising diaphragmatic wall means operable to actuate said valve means, said container means comprising a bottom wall which constitutes said diaphragmatic wall means, said container means having side wall extending from said bottom wall, said bottom wall being integral with said side wall.

17. As aspirating device for removing fluids from a body site, comprising container means for collecting aspirated fluids, suction means in communication with said container means for applying a negative pressure to said container means, tube means connected to said container means and adapted to communicate with a body site for transferring fluids from said body site to said container means in response to negative pressure in said container means, and valve means for controlling the negative pressure in said container means, said container means comprising diaphragmatic wall means operable to actuate said valve means, said valve means comprising an actuatable valve mounted on said container means, said actuatable valve having a valve passage extending between the inside and outside of said container means, said actuatable valve comprising an actuatable member operable in said valve passage between an unactuated position and an actuated position, said actuatable member blocking said valve passage when in said unactuated position, said actuatable member unblocking said valve passage when in said actuated position and thereby being operable to admit ambient air through said valve passage into said container means to reduce the extend of negative pressure in said container means when in said actuated position.

18. An aspirating device for removing fluids from a body site, comprising container means for collecting aspirated fluids, suction means in communication with said container means for applying a negative pressure to said container means, tube means connected to said container means and adapted to communicate with a body site for transferring fluids from said body site to said container means in response to negative pressure in said container means, and valve means for controlling the negative pressure in said container means, said container means comprising diaphragmatic wall means operable to actuate said valve means, said container means having a side wall, said diaphagmatic wall means being a bottom wall integral with said side wall, said bottom wall having an upright stem for actuating said valve means, said stem being integral with said bottom wall.

* * * * *